United States Patent [19]

Kelman

[11] Patent Number: 4,710,194

[45] Date of Patent: Dec. 1, 1987

[54] INTRAOCULAR LENS WITH OPTIC OF EXPANDABLE HYDROPHILIC MATERIAL

[76] Inventor: Charles D. Kelman, 269 Grand Central Pkwy., Floral Park, N.Y. 11005

[21] Appl. No.: 921,227

[22] Filed: Oct. 20, 1986

[51] Int. Cl.⁴ .............................................. A61F 2/16
[52] U.S. Cl. ....................................................... 623/6
[58] Field of Search ............................................ 623/6

[56] References Cited

U.S. PATENT DOCUMENTS

| | | | |
|---|---|---|---|
| 4,373,218 | 2/1983 | Schachar | 623/6 |
| 4,449,257 | 5/1984 | Koeniger | 623/6 |
| 4,556,998 | 12/1985 | Siepser | 623/6 |
| 4,585,457 | 4/1986 | Kalb | 623/6 |
| 4,615,702 | 10/1986 | Koziol et al. | 623/6 |

Primary Examiner—Ronald L. Frinks
Attorney, Agent, or Firm—Henry Sternberg

[57] ABSTRACT

An intraocular lens having a hydrophilic optical element. The hydrophilic material of the optical element is capable of being hydrated by the natural fluid in the eye to expand after implantation to provide an optically correct lens of suitable diameter, to permit implantation of the lens through an incision of minimal length corresponding to the diameter of the dry lens and thus restoring the vision of the patient with minimal trauma. The lens includes position-fixation members and connecting means for securing the hydrophilic optic to the position-fixation member. The position-fixation members are connected to the hydrophilic optic element in such manner that the lens can be seated in the eye prior to expansion of the hydrophilic optic and expansion after seating does not impact substantial movement to the position-fixation members. The invention also includes the improved method of implantation through an incision of minimal length.

18 Claims, 5 Drawing Figures

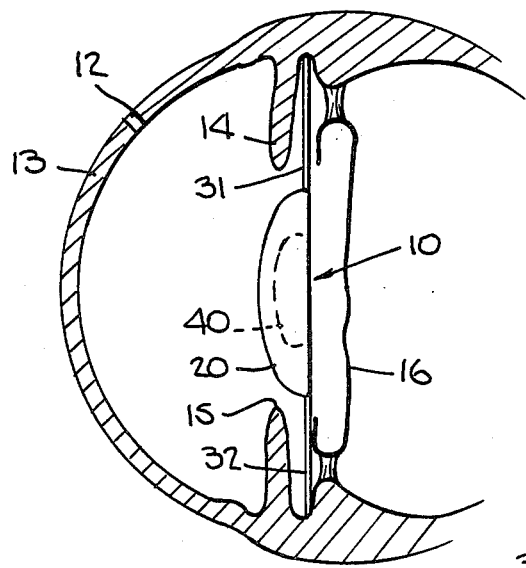
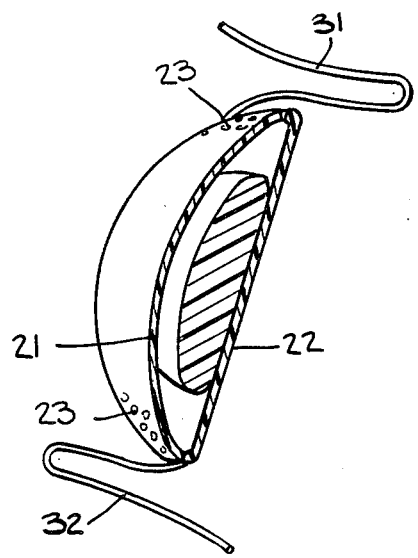
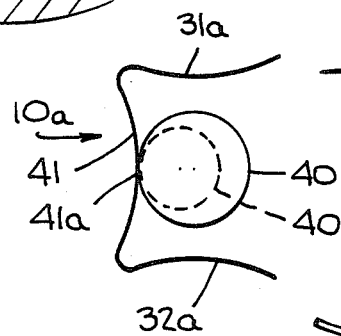
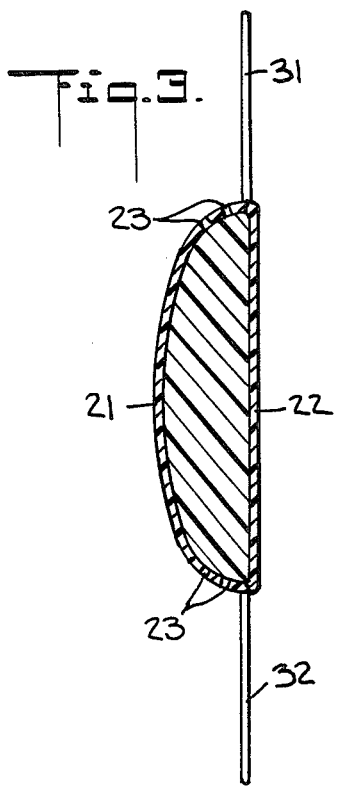
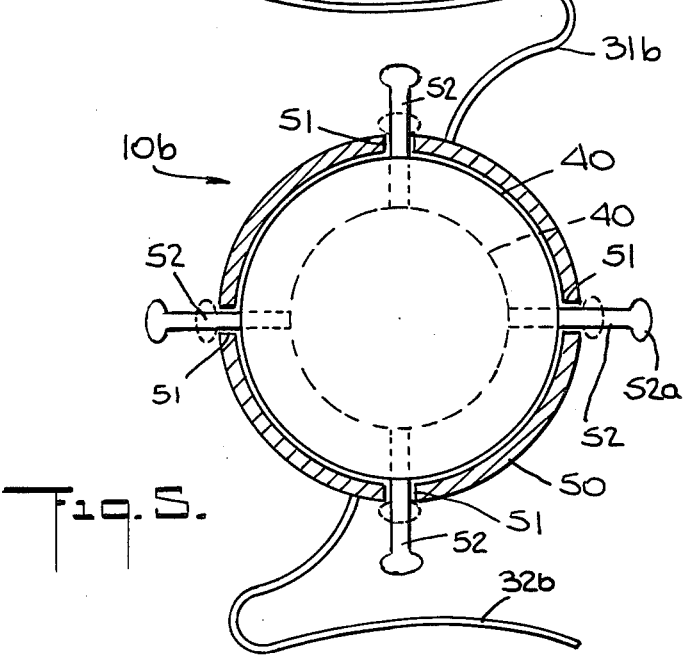

INTRAOCULAR LENS WITH OPTIC OF EXPANDABLE HYDROPHILIC MATERIAL

BACKGROUND OF THE INVENTION

This invention relates to an intraocular lens for use as an artificial lens implant after surgical removal of a cataracted human lens from an eye. More particularly, to an intraocular lens which may be inserted through an incision much smaller than that ordinarily required for insertion of known intraocular lenses of this type.

Heretofore, there have been known intraocular lenses of many types, generally having a medial light-focusing lens body for focusing light on the retina of the eye and a pair of haptics extending from opposite peripheral regions of the lens body for seating the lens in the eye in proper relation to the pupil. The lens body is typically of such material and of such configuration that it exhibits the proper optical characteristics for focusing light on the retina of the eye in which it is to be seated. The known intraocular lenses are made of materials such as, for example, polymethylmethacrilate (PMMA) which are inert with respect to the fluids and tissue within the eye and are inserted into the eye through an incision which is typically at least as large as the smallest diameter of the lens body, or optic, of the lens in question.

Recently, several attempts have been made to develop lenses whose lens bodies are deformable so that they may be inserted through a smaller incision than that previously required. One such known lens has both its optic and haptic portions made of Hema. The known Hema lens has the general shape of the Choyce lens, i.e. a generally rectangular, flat, lens, having a central optic portion and flat sheet-like haptic portions extending from opposite peripheral regions of the optic portion. The lens (i.e. both the optic and the haptic) is fabricated with the Hema material in dry, i.e. dehydrated, and thus contracted condition. The dehydrated lens can be readily inserted through a small incision in the eye. Thereafter, the Hema material slowly absorbs the fluid in the eye and slowly expands to its desired shape. The grave disadvantage of such lenses is that the haptics, since they are also formed of Hema, are also in contracted, i.e. dehydrated, condition at the time of insertion and it takes a considerable amount of time for the haptics to return to their desired expanded shape and size. Such haptics, cannot be properly seated until they are back in expanded condition. The eye incision, therefore, cannot be closed until the haptics have returned to their original expanded shape and are known to be properly seated. The prolongation of the surgical procedure necessitated by such known Hema lens construction inevitably increases the risk of complication.

Another known intraocular lens of Hema is the one disclosed in U.S. Pat. No. 4,449,257 issued May 22, 1984. The latter patent teaches a Hema lens which is shaped specifically for implantation and retention in the posterior capsule and held in place therein by concentric grooves cut in the marginal peripheral portion of the lens. While the Hema optic may, according to this latter patent, be inserted into the eye through a relatively small incision, several disadvantages are believed to result. First, in order to be certain of proper seating of the lens (which has no haptics extending therefrom) it would appear that the incision must be kept open until the Hema optic has expanded to substantially its final enlarged condition, since it is only then that such lens may be properly seated. Secondly, the lens in question can only be used in the posterior capsule and cannot be seated in any other portion of the posterior or anterior chamber. Thirdly, the Hema optic according to U.S. Pat. No. 4,449,257 can only be used in an eye in which the posterior capsule is in reasonably good condition and sufficient portions thereof remain in tact for retaining the optic in place. Lastly, the Hema optic according to the latter patent must be sized such that it will fill the particular posterior capsule of the patient in question, since if it expands to too large a size it may damage the posterior capsule, while on the other hand, if its expanded size is too small, it may not seat properly.

It would, of course, be highly advantageous to be able to reduce not only the size of the incision but also to reduce the length of time required for performing the surgical procedure. By doing so the patient's recovery would be speeded and the possibility of complications resulting from the surgery would be minimized.

SUMMARY OF THE INVENTION

It is therefore an object of the present invention to provide a practical means and method which obviate the disadvantages encountered with the prior art structures described above.

It is also a primary object of the present invention to provide an intraocular lens whose optic may be in contracted condition so as to pass through an incision of much smaller size than that now typically required.

It is another object of the invention to provide an intraocular lens of the above type which is such that the optic, once it has been inserted into the eye, will readily expand to a predetermined shape suitable to provide the optical characteristics for the particular eye in question.

It is a further object of the invention to provide an intraocular lens of the above type in which the structure is such that the incision need not be kept open any longer than currently required for seating of the haptics of conventional intraocular lenses.

It is a concomitant object of the invention to provide a new and novel method for inserting and seating an intraocular lens in the eye.

In accordance with the present invention, there is provided an intraocular lens comprising a medial lens body of hydrophilic material, for focusing light rays on the retina. The lens body is expandable in response to hydration thereof. The lens further comprises positioning means cooperating with the lens body for seating the lens in the eye. The positioning means are constructed, preferably of non-hydrophilic material, such that their shape and resilience is not substantially affected by the fluid in the eye. Connecting means are provided for securing the lens body with respect to the positioning means so that when the latter are seated in the eye, and the lens body has expanded, the latter will be in light focusing position in relation to the pupil. According to the invention, the hydrophilic material of the optic is cut and shaped when dry to a shape that will expand with the uptake of aqueous humor in the eye to an expanded condition in which the optic exhibits the desired optical characteristics.

The foregoing objects, as well as the characteristic features of the invention, will become more apparent and readily understandable by the following description and the appended claims when read in conjunction with the accompanying drawings.

BRIEF DESCRIPTION OF THE DRAWINGS

FIG. 1, is a transverse sectional view of the anterior portion of an eye showing the lens of the invention after seating thereof in the posterior chamber, with the optic shown both dry and after aqueous humor uptake;

FIG. 2, is an enlarged fragmentary sectional perspective view of the lens according to the present invention showing the optic in dry condition prior to uptake of aqueous humor;

FIG. 3, is an enlarged, transverse sectional view of the lens after uptake by the optic of aqueous humor;

FIG. 4, is a front plan view of a lens according to another preferred embodiment of the invention; and FIG. 5 is a front plan view of still another preferred embodiment of a lens according to the present invention.

DETAILED DESCRIPTION OF THE PREFERRED EMBODIMENT

Referring to FIGS. 1-3, the lens 10 of the invention comprises a medial sac 20, a position-fixation means comprising a pair of position-fixation elements 31,32 in the form of a pair of haptics extending from opposite peripheral portions of the sac 20, and an optic 40 of hydrophilic material, for example, Hema (Polyhydroxy-ethylene thacrylate) with a water uptake of between 45% and 70%. Preferably, the sac 20 is in the form of a pair of thin circular sheets of transparent silicone rubber, connected at their periphery to form the sac and having a plurality of small openings 23 distributed around the periphery thereof for permitting exchange of fluid between the interior and the exterior of the sac.

The Hema optic 40 is preferably round. It is cut and shaped with the Hema in dry condition, to a size, proportional to the amount of expansion expected in response to water uptake. The dry tablet 40 of Hema, is inserted into the sac 20 prior to final sealing of the sheets 21,22 forming the sac.

The lens 10 is inserted "dry" (see FIG. 2) into the eye through a corneo scleral incision 12 in the cornea 13 of an eye having an iris 14, a pupil 15, and a posterior capsule 16. The corneo scleral incision 12 need be no larger than is required for an object the size of the dry Hema optic 40, since the sac 20 can be readily collapsed to snugly surround the dry Hema optic 40. The sheets 21,22 forming the sac 20 are relatively thin so that when sac 20 is collapsed and wrapped about the dry Hema optic, therein, the material of the sac does not substantially add to the outer diameter of the optic, so that the lens may be inserted through the aforesaid minimum size incision 12.

Sac 20 is preferably preshaped to substantially correspond to the outer configuration which the expanded optic 40 will posses. The shape and material of sac 20 is preferably chosen such that the latter exhibits a "memory", which causes it to return to the preformed initial shape thereof after external deforming forces thereon have been removed. Thus, prior to insertion of the lens into an eye, the membranes 21 and 22 may be first squeezed toward and into contact with the contracted, dry, Hema optic located therebetween, and curled around it for decreasing the size of the overall unit for purposes of insertion through a minimum size incision. The "memory" of the sac 20 causes it to return to its initial, undeformed, configuration after it has been inserted in the eye and the forcepts or other instrument retaining it in deformed condition has been removed. Since the sac is hollow and communicates with the atmosphere through the perforations 23, it is relatively easy to squeeze the membranes together and wrap them about the smaller, dry, Hema optic located therebetween and then insert the thusly deformed lens into the eye through a relatively small incision 12.

While silicone is a preferred material for forming the sac 20, any other material may be used which has suitable optical properties, is similarly deformably, has a memory tending to return the structure to its original condition and is relatively inert with respect to the fluids and tissues within the eye.

Preferably, the sheets 21,22 forming the sac 20, are sufficiently thin so as to form only a receptacle for and not affect the optical properties of, the Hema optic 40 therein.

Implantation of the lens according to the present invention is preferably accomplished as follows. The lens 10 is preferably inserted into the eye with the sac 20 "wrapped" (not shown) about the contracted optic 40. Once in the eye, the instrument used to retain sac 20 in "wrapped" condition, is removed and sac 20 is permitted to snap back to its initial condition. The lens is then seated by way of the haptics 31,32 in proper position in the eye, for example, in the posterior chamber position shown in FIG. 1. It will be seen that haptics 31,32 which are preferably formed of non-hydrophilic material, so as to have a shape and resilience substantially unaffected by the fluid in the eye, are fully extended and ready for final seating as soon as sac 20 has snapped back to its initial, undeformed, condition. Meanwhile, aqueous humor enters the interior chamber of sac 20 through the openings 23 to fill such chamber.

Uptake of aqueous humor of the eye expands the optic 40 from its original insertion size, as shown in broken lines in FIG. 1, to fill the sac 20, as seen in FIG. 3.

It will be seen that while uptake of aqueous humor only begins after the lens has been inserted into the eye, seating of the lens may immediately proceed and the incision may be sutured as soon as seating has been completed, without the need to wait for the optic 40 to have achieved its full desired size, i.e. the fully hydrated size seen in FIG. 3, and, in full lines, in FIG. 1.

Accordingly, the present invention provides an improved intraocular lens which is capable of being inserted through an incision in an eye of less than 3 millimeters in length while having an optic which expands to standard 5 millimeter or 6 millimeter diameter size, after implantation in the eye.

Both the optic 40 and the sac 20 preferably have a convex anterior and a generally flat posterior surface as depicted in FIG. 3, when in final, expanded, condition. The membranes 21,22 are preferably less than about 1 millimeter in thickness.

FIG. 4 illustrates another preferred embodiment of the invention. Intraocular lens 10a comprises a pair of position-fixation members 31a, 32a connected to opposite ends, respectively, of an elongated intermediate member 41. Member 41 is tangent to a point on the periphery of a dry Hema optic 40. The optic 40 is generally round and preferably has a convex anterior and a generally flat posterior surface. The shape of the dry Hema optic is illustrated by broken lines in FIG. 4. After insertion into the eye the uptake of aqueous humor of the eye softens and expands the optic 40 from its original insertion size shown in broken lines to the final size shown in full lines in FIG. 4. It will be seen that the lens 10a may be inserted in dry condition into the eye and immediately seated therein without having to wait for optic 40 to expand to its final size, since the haptics 31a, 32a are unaffected by the size, i.e. amount of liquid uptake, of the Hema optic. The haptics 31a, 32a may be PMMA or Prolene and are preferably connected to the optic 40 at the point 41a which is preferably centrally located along member 41, which latter is tangential with respect to the circumference of the optic.

A still further preferred embodiment of the present invention is shown in FIG. 5 where a Hema optic 40 is again shown in "dry" condition by broken lines, representing its insertion size. Uptake of the aqueous humor of the eye softens and expands the optic 40 from its original insertion size, as shown in broken lines, to the final size shown in full lines in FIG. 5. Bonded to the Hema optic at points distributed along the periphery of the optic, approximately 90° apart, are Prolene rods extending radially from the optic. Each of these Prolene rods extends through a corresponding one of a plurality of radial bores 51 distributed at approximately 90° intervals along the circumference of an outer ring 50, preferably also of Prolene, surrounding the optic 40. Optic 40 is held in place only by the four rods 52 extending through outer ring 50 which latter has extending from opposite peripheral portions thereof a pair of haptics 31b and 32b of conventional construction. Each of the rods 52 is bonded at the radially inner end thereof to the periphery of the optic and is preferably provided with a bulbous portion 52a at its outer axial end thereof, outwardly of the ring 50 for preventing the ends of the rods being withdrawn inwardly through the bores 51. Preferably, the rods 52 are slightly curved (not shown) out of the plane of the paper in which they are illustrated in FIG. 5 and are slidingly received in the corresponding radial bores 51 of the ring 50. The ring 50, as well as the rods 52 being of a material such a Prolene, can be readily squeezed together into a relatively small shape, around the contracted dry optic, for insertion of the assembled lens 10b through the relatively small corneo scleral incision 12.

While shown in exaggerated size in FIG. 5, it will be understood that the ring 50 preferably has an inner diameter generally corresponding in size to the outer diameter of the optic 40, when the latter is in its final expanded condition so as to be substantially supported therein.

In use, the lens 10b is inserted into the eye after the ring 50 and the rods 52 have been squeezed together around the dry Hema optic. After the lens is inside the eye the resilient ring 50 and rods 52 snap back to their original shape so that the lens may be immediately seated in the eye. Meanwhile, uptake of aqueous humor of the eye softens and expands the optic 40 from its original insertion size, as shown in broken lines, to the full line condition seen in FIG. 5. This process begins as soon as the lens has been inserted into the eye and may continue after closing of the incision 12 after seating of the lens. Expansion of the dry Hema optic from the broken line to the solid line condition thereof, results in radially outward movement of each of the rods 52, through the corresponding bores 51 resulting also in movement of the bulbous end portions 52a from their initial position shown in broken lines to the position thereof shown in full lines in FIG. 5. It will be seen that the rod/ring structure maintains the optic 40 centrally located with respect to the haptics, during and after expansion of the optic from its dry, contracted, condition to its fully expanded, operative condition.

The slight curvature of the rods (not shown) is preferably provided for minimizing the risk that the rods in their radially outermost position will come in contact with any tissue within the eye. The outer ring 50 is preferably of square cross-section and approximately 1 millimeter in thickness and preferably has an inner diameter of approximately 6 millimeters.

Although the foregoing detailed description has been made exclusively with reference to the preferred embodiment of the invention, it should be understood that the preferred embodiment as described and shown herein is not intended in any way to be a limitation of the present invention, but on the contrary, many changes, variations, and modifications with respect to the construction and arrangement in practice thereof may further be derived by those skilled in the art to which the present invention pertains.

What is claimed is:

1. An intraocular lens for implantation in a human eye, comprising:

optic means of hydrophilic material adapted to be in contracted condition when dry and to expand to an expanded condition in response to uptake of liquid from the environment, said hydrophilic optic means being formed to such a size and shape, in dry contracted condition thereof, that it will have the desired optical characteristic when in final expanded condition thereof;

position-fixation means for seating the lens in the eye, said position-fixation means being constructed of substantially non-hydrophilic material so as to retain their shape and resiliency characteristics substantially independently of the liquid environment within the eye; and connecting means for securing said hydrophilic optic means to said position-fixation means, said connecting means being adapted to position said hydrophilic optic means generally centrally with respect to the optical axis of the eye, when said hydrophilic optic means is in said expanded condition thereof, and to permit seating of said position fixation means within the eye irrespective of the size of said hydrophilic optic means between said contracted and expanded conditions thereof, said connecting means comprising a medial sac of pliable, optically transparent, material defining an interior chamber centrally located with respect to said position-fixation means and adapted to receive therein said hydrophilic optic means in dry condition thereof, said medial sac having openings therein for allowing aqueous humor of the eye to enter into the interior of the sac after insertion of the lens into the eye and said sac being adapted to maintain said optic means substantially centrally positioned with respect to the optical axis of the eye after said optic means is in fully expanded condition thereof, said connecting means further comprising means integrally connecting said position-fixation means with said medial sac.

2. An intraocular lens according to claim 1 wherein the material of said hydrophylic optic means is Hema.

3. An intraocular lens according to claim 1 wherein said sac is substantially the shape of said optic means when the latter is in expanded condition thereof, said sac being deformable to a smaller configuration for insertion thereof through a relatively small incision into the eye and adapted to return to its initial undeformed condition upon release of the external deforming forces thereon.

4. An intraocular lens according to claim 1, wherein said openings are perforations distributed around the periphery of said medial sac.

5. An intraocular lens according to claim 1, wherein said medial sac is formed of silicone rubber.

6. An intraocular lens according to claim 1, wherein said position-fixation means includes a pair of position-fixation means extending generally from diametrically opposite peripheral regions of said sac.

7. An intraocular lens according to claim 1, wherein said optic means comprises a Hema material with between 45% and 70% liquid uptake.

8. An intraocular lens according to claim 7, wherein said Hema optic means is, when in dry contracted condition, of a size and shape proportional to the size and shape of the Hema optic means when the latter is in final expanded condition thereof, said proportion being chosen in relation to the amount of expansion expected for the specific Hema material, in response to fluid uptake in order to achieve the desired final size and shape for the optic.

9. An intraocular lens for implantation in a human eye, comprising:
  optic means of hydrophilic material adapted to be in contracted condition when dry and to expand to an expanded condition in response to uptake of liquid from the environment, said hydrophilic optic means being formed to such a size and shape, in dry contracted condition thereof, that it will have the desired optical characteristics when in final expanded condition thereof;
  position-fixation means for seating the lens in the eye, said position-fixation means being constructed of substantially non-hydrophilic material so as to retain their shape and resiliency characteristics substantially independently of the liquid environment within the eye; and
  connecting means for securing said hydrophilic optic means to said position-fixation means, said connecting means being adapted to position said hydrophilic optic means generally centrally with respect to the optical axis of the eye, when said hydrophilic optic means is in said expanded condition thereof, and to permit seating of said position-fixation means within the eye irrespective of the size of said hydrophilic optic means between said contracted and expanded conditions thereof,
  said position-fixation means comprising a pair of generally diametrically opposed position-fixation members and an intermediate member connecting said opposed position-fixation members, said intermediate member having a central portion generally tangentially juxtaposed with a peripheral portion of said optic means, and said connecting means including means integrally connecting said central portion of said position-fixation means with said peripheral portion of said optic means, whereby said optic means is free to expand from its initial dry condition to its fully expanded condition upon uptake of liquid, while maintaining its generally central location with respect to said opposed pair of position-fixation members.

10. An intraocular lens according to claim 9, wherein said connecting means is a bonding material for bonding said optic means to said position-fixation means.

11. An intraocular lens for implantation in a human eye, comprising:
  optic means of hydrophilic material adapted to be in contracted condition when dry and to expand to an expanded condition in response to uptake of liquid from the environment, said hydrophilic optic means being formed to such a size and shape, in dry contracted condition thereof, that it will have the desired optical characteristics when in final expanded condition thereof;
  position-fixation means for seating the lens in the eye, said position-fixation means being constructed of substantially non-hydrophilic material so as to retain their shape and resiliency characteristics substantially independently of the liquid environment within the eye; and
  connecting means for securing said hydrophilic optic means to said position-fixation means, said connecting means being adapted to position said hydrophilic optic means generally centrally with respect to the optical axis of the eye, when said hydrophilic optic means is in said expanded condition thereof, and to permit seating of said position fixation means within the eye irrespective of the size of said hydrophilic optic means between said contracted and expanded conditions thereof,
  said optic means having a circular outer periphery and said connecting means comprising an outer annular ring member of resiliently deformable material surrounding said optic means and having a plurality of radial bores extending therethrough, a plurality of radially positioned rod means extending through respective ones of said bores, each said rod means having an inner axial end portion integrally connected with a corresponding peripheral region of said optic means, and said position-fixation means integrally connected with said annular ring means.

12. An intraocular lens according to claim 11, wherein said annular ring means for an inner diameter substantially equal to the outer diameter of said optic means and surrounding the latter, for centrally locating the optic means with respect thereto.

13. An intraocular lens according to claim 11, wherein each of said rod means has an enlarged portion at the outer axial end thereof outwardly of said annular ring member.

14. Method of seating an intraocular lens in a human eye whose cataracted natural lens has been removed, comprising the steps of:
  forming a dry contracted optic of hydrophilic material to a size and shape such that when it expands upon aqueous humor uptake it will be of the size and shape of the optic desired for the patient in question;
  securing the optic to position-fixation means of non-hydrophilic material, including forming a sac of pliable transparent material having an interior chamber of a size and shape substantially corresponding to the size and shape of the expanded optic desired and having a memory with respect to that shape allowing the sac to return to that shape when external forces thereon are removed, and positioning said dry hydrophilic optic in said interior chamber of said sac and closing said sac therearound;

inserting the lens into the interior of the eye through an incision in the eye;

seating the position-fixation means of the lens in the eye;

closing the incision, and thereafter, allowing the optic to expand to its final expanded condition in response to uptake of fluid within the eye, maintaining the optic generally centrally located with respect to the optical axis of the eye after the optic has reached its final expanded condition.

15. The method according to claim 14 wherein the step of allowing the optic to expand, comprises providing access openings in said sac through which the interior of said sac communicates with the environment at the exterior thereof;

allowing the fluid in the eye to enter into the interior chamber of said sac; and allowing the dry and contracted hydrophilic optic to uptake fluid and expand to its final expanded condition substantially filling said sac and engaging the interior walls thereof for insuring that said optic, in expanded condition, is substantially centrally located with respect to the optical axis of the eye.

16. The method according to claim 14, wherein the material of said optic is Hema and said step of inserting the lens into the eye comprises deforming the sac around the dry contracted Hema optic positioned therein, for insertion of the lens through an incision of a size not substantially in excess of the diameter of the Hema optic when the latter is in dry contracted condition thereof.

17. The method according to claim 14 wherein the step of seating the lens within the eye occurs prior to said hydrophilic material of said optic being fully expanded to final expanded condition thereof.

18. An intraocular lens for implantation in a human eye, comprising:

optic means of hydrophilic material adapted to be in contracted condition when dry and to expand to an expanded condition in response to uptake of liquid from the environment, said hydrophilic optic means being formed to such a size and shape, in dry contracted condition thereof, that it will have the desired optical characteristics when in final expanded condition thereof;

position-fixation means for seating the lens in the eye, said position-fixation means being constructed of substantially non-hydrophilic material so as to retain their shape and resiliency characteristics substantially independently of the liquid environment within the eye; and connecting means for securing said hydrophilic optic means to said position-fixation means, said connecting means being constructed to permit expansion of said optic means from contracted to expanded condition thereof without resulting in any substantial movement being imparted to said position-fixation means, said connecting means being adapted to position said hydrophilic optic means generally centrally with respect to the optical axis of the eye, when said hydrophilic optic means is in said expanded condition thereof, and to permit seating of said position-fixation means within the eye irrespective of the size of said hydrophilic optic means between said contracted and expanded conditions thereof.

* * * * *

UNITED STATES PATENT AND TRADEMARK OFFICE
CERTIFICATE OF CORRECTION

PATENT NO. : 4,710,194

DATED : December 1, 1987

INVENTOR(S) : Charles D. Kelman

It is certified that error appears in the above-identified patent and that said Letters Patent is hereby corrected as shown below:

Column 8, claim 12, line 44, delete "for" and substitute therefor --has--.

Signed and Sealed this

Twenty-sixth Day of April, 1988

Attest:

DONALD J. QUIGG

Attesting Officer     Commissioner of Patents and Trademarks